(12) United States Patent
Nishizawa et al.

(10) Patent No.: US 8,093,395 B2
(45) Date of Patent: Jan. 10, 2012

(54) SPHINGOSINE COMPOUND, METHOD FOR PRODUCING THE SAME, AND SPHINGOMYELINASE INHIBITOR

(75) Inventors: Mugio Nishizawa, Tokushima (JP); Hiroshi Imagawa, Tokushima (JP); Jun Sakurai, Tokushima (JP); Masataka Oda, Tokushima (JP)

(73) Assignee: Otsuka Chemical Co., Ltd., Osaka-Shi (JP)

( * ) Notice: Subject to any disclaimer, the term of this patent is extended or adjusted under 35 U.S.C. 154(b) by 217 days.

(21) Appl. No.: 12/530,311

(22) PCT Filed: Mar. 5, 2008

(86) PCT No.: PCT/JP2008/053936
§ 371 (c)(1), (2), (4) Date: Dec. 7, 2009

(87) PCT Pub. No.: WO2008/111450
PCT Pub. Date: Sep. 18, 2008

(65) Prior Publication Data
US 2010/0099881 A1 Apr. 22, 2010

(30) Foreign Application Priority Data
Mar. 9, 2007 (JP) .................................. 2007-60950

(51) Int. Cl.
*C07D 211/70* (2006.01)
*A61K 31/44* (2006.01)
(52) U.S. Cl. ....................................... 546/348; 514/332
(58) Field of Classification Search ........................ None
See application file for complete search history.

(56) References Cited

FOREIGN PATENT DOCUMENTS

| JP | 2000-86601 | | 3/2000 |
|---|---|---|---|
| JP | 2001-213858 | A1 | 8/2001 |
| JP | 2004-175735 | A1 | 6/2004 |
| JP | 2005-281209 | A1 | 10/2005 |
| WO | WO 01/38295 | A1 | 5/2001 |

OTHER PUBLICATIONS

M. Taguchi, et al.; "Sphingomyelin Analogues as Inhibitors of Sphingomyelinase;" Bioorganic & Medicinal Chemistry Letters; vol. 13; 2003; pp. 1963-1966.
International Search Report for International Application No. PCT/JP2008/053936 dated Apr. 8, 2008.

*Primary Examiner* — Janet Andres
*Assistant Examiner* — Heidi Reese
(74) *Attorney, Agent, or Firm* — Kratz, Quintos & Hanson, LLP

(57) ABSTRACT

An object of the invention is to provide a novel sphingosine compound with an inhibitory activity against sphingomyelinase, and a method for producing the sphingosine compound.
The novel sphingosine compound or a salt thereof according to the invention is represented by Formula (1):

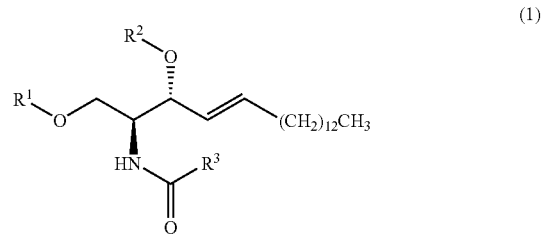

wherein one of $R^1$ and $R^2$ is hydrogen, and the other is a group represented by Formula (G):

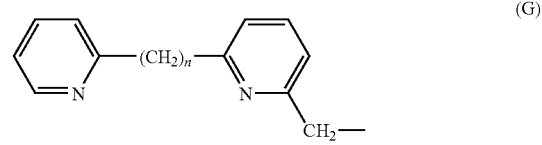

wherein n is 0 or 1; and $R^3$ is hydrogen, $C_{1-23}$ alkyl, $C_{3-8}$ cycloalkyl, $C_{2-6}$ alkenyl, $C_{1-6}$ alkoxy, $C_{3-8}$ cycloalkyloxy, phenyl, or furil.

5 Claims, No Drawings

SPHINGOSINE COMPOUND, METHOD FOR PRODUCING THE SAME, AND SPHINGOMYELINASE INHIBITOR

TECHNICAL FIELD

The present invention relates to a sphingosine compound, a method for producing the sphingosine compound, and a sphingomyelinase inhibitor.

BACKGROUND ART

Sphingomyelinase, also known as sphingomyelin phosphodiesterase, is a type of phospholipase that breaks down the substrate sphingomyelin, which is a type of membrane lipid, into ceramide and phosphocholine. Sphingomyelinase is believed to play an important role in regulating the sphingomyelin metabolic pathway in vivo.

Sphingomyelinase is activated by extracellular cytokines, hormones, and the like. Ceramide thus produced is believed to play an important role as a lipid second messenger in various cellular functions, such as apoptosis, cell proliferation, differentiation, etc. This signal transduction pathway is referred to as the sphingomyelin pathway, and physiologically active substances known to be involved in this pathway are cell adhesion molecules such as tumor necrosis factor (TNF-α), interleukin 1β (IL-1β), and like cytokines, Fas, D28, CD40-ligand, etc. These in vivo physiologically active substances are believed to be deeply involved in the onset of various diseases or the expression of various life phenomena, such as inflammation, cell death, immune system control, etc. This indicates the importance of the sphingomyelin pathway in vivo.

Sphingomyelinase-specific inhibitors are promising drugs for the prevention and treatment of cerebral hemorrhage, cerebral infarction, and like cerebrovascular diseases, head injuries, senile dementia represented by Parkinson's disease and Alzheimer's disease, and like neurodegenerative diseases, diabetes, obesity, arteriosclerosis, inflammatory diseases, immune diseases, cancer, renal diseases, and cardiac diseases. Thus, many sphingomyelinase inhibitors have been proposed (PTL 1 to 4).

However, no sphingomyelinase inhibitor has been developed that is effective for patients of senile dementia, the population of which is expected to increase in the future.

CITATION LIST

Patent Literature

[PTL 1] Japanese Unexamined Patent Publication No. 2000-86601
[PTL 2] Japanese Unexamined Patent Publication No. 2001-213858
[PTL 3] Japanese Unexamined Patent Publication No. 2004-175735
[PTL 4] Japanese Unexamined Patent Publication No. 2005-281209

SUMMARY OF INVENTION

Technical Problem

An object of the invention is to provide a novel sphingosine compound with an inhibitory activity against sphingomyelinase, and a method for producing the sphingosine compound.

Solution to Problem

The present inventors conducted extensive research to solve the above-described object, and consequently found that a sphingosine compound which was first synthesized by the inventors exhibits a potent inhibitory activity against sphingomyelinase. The invention was accomplished based on this finding.

The invention provides a sphingomyelinase compound, a method for producing the sphingomyelinase compound, and a sphingomyelinase inhibitor containing the sphingomyelinase compound, as summarized in Items 1 to 5 below.

Item 1: A sphingosine compound or a salt thereof represented by Formula (1):

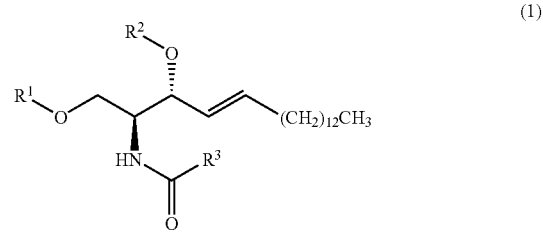

wherein one of $R^1$ and $R^2$ is hydrogen, and the other is a group represented by Formula (G):

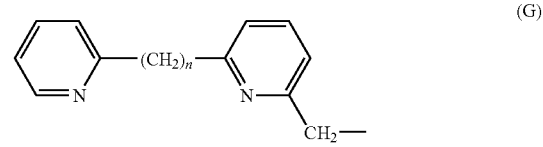

wherein n is 0 or 1; and $R^3$ is hydrogen, $C_{1-23}$ alkyl, $C_{3-8}$ cycloalkyl, $C_{2-6}$ alkenyl, $C_{1-6}$ alkoxy, $C_{3-8}$ cycloalkyloxy, phenyl, or furil.

Item 2: The sphingosine compound or a salt thereof according to Item 1, wherein $R^1$ is a group represented by Formula (G), and $R^2$ is hydrogen.

Item 3: The sphingosine compound or a salt thereof according to Item 1, wherein $R^1$ is hydrogen, and $R^2$ is a group represented by Formula (G).

Item 4: A method for producing a sphingosine compound or a salt thereof represented by Formula (1):

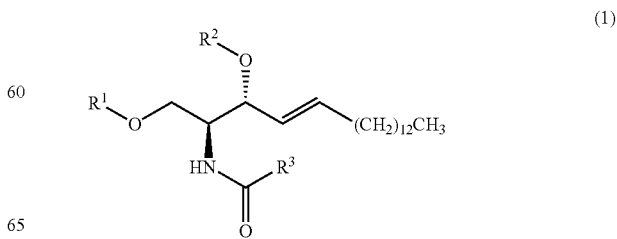

wherein one of $R^1$ and $R^2$ is hydrogen, and the other is a group represented by Formula (G):

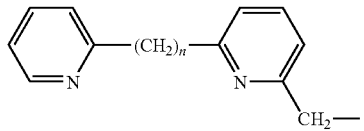
(G)

wherein n is 0 or 1; and $R^3$ is hydrogen, $C_{1-23}$ alkyl, $C_{3-8}$ cycloalkyl, $C_{2-6}$ alkenyl, $C_{1-6}$ alkoxy, $C_{3-8}$ cycloalkyloxy, phenyl, or furil; the method comprising:
reacting a tin oxide compound with a compound represented by Formula (2):

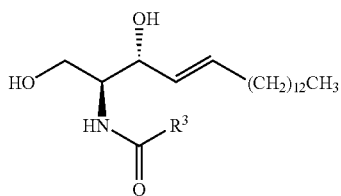
(2)

wherein $R^3$ is hydrogen, $C_{1-23}$ alkyl, $C_{3-8}$ cycloalkyl, $C_{2-6}$ alkenyl, $C_{1-6}$ alkoxy, $C_{3-8}$ cycloalkyloxy, phenyl, or furil; and
reacting the resulting compound with a bipyridyl compound represented by Formula (3):

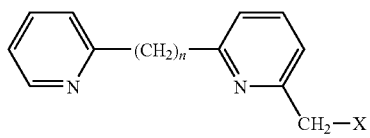
(3)

wherein n is 0 or 1, and X is halogen.

Item 5: A sphingomyelinase inhibitor containing a sphingosine compound or a salt thereof represented by Formula (1):

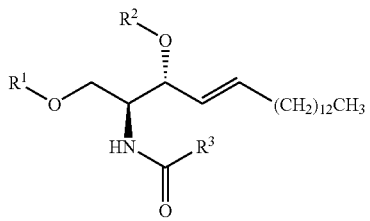
(1)

wherein one of $R^1$ and $R^2$ is hydrogen, and the other is a group represented by Formula (G):

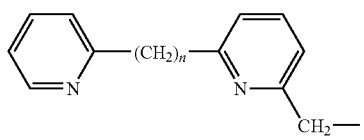
(G)

wherein n is 0 or 1; and $R^3$ is hydrogen, $C_{1-23}$ alkyl, $C_{3-8}$ cycloalkyl, $C_{2-6}$ alkenyl, $C_{1-6}$ alkoxy, $C_{3-8}$ cycloalkyloxy, phenyl, or furil.

The sphingosine compound of the invention is represented by Formula (1):

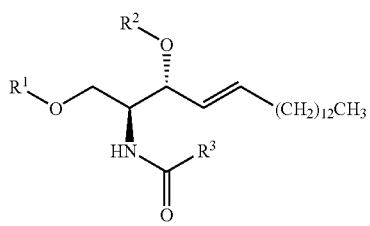
(1)

wherein $R^1$, $R^2$ and $R^3$ are as defined above.

In Formula (1), one of $R^1$ and $R^2$ is hydrogen, and the other is a substituent represented by Formula (G):

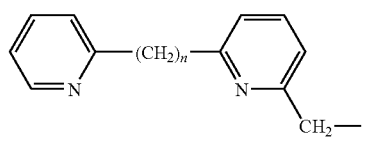
(G)

wherein n is 0 or 1.

The sphingosine compound represented by Formula (1) encompasses the sphingosine compounds represented by Formulae (1A) and (1B):

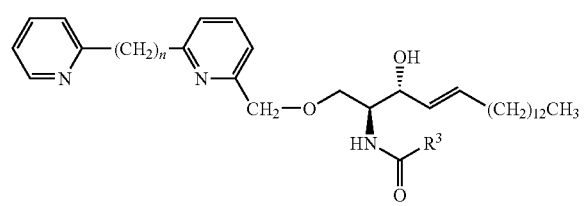
(1A)

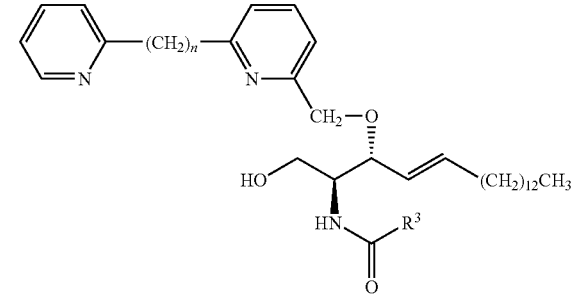
(1B)

wherein n and $R^3$ are as defined above.

Compounds represented by Formulae (1A) and (1B) wherein n is 0 are preferred.

The sphingosine compounds represented by Formula (1A) are preferred.

Examples of $C_{1-23}$ alkyl represented by $R^3$ in Formula (1) include $C_{1-23}$ straight- or branched-chain alkyl, such as methyl, ethyl, n-propyl, isopropyl, n-butyl, isobutyl, sec-butyl, tert-butyl, n-pentyl, isopentyl, neopentyl, tert-pentyl, n-hexyl, isohexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, etc.

Examples of $C_{3-8}$ cycloalkyl represented by $R^3$ in Formula (1) include $C_{3-8}$ cycloalkyl, such as cyclopropyl, cyclobutyl, cyclopentyl, cyclohexyl, cycloheptyl, cyclooctyl, etc.

Examples of $C_{2-6}$ alkenyl represented by $R^3$ in Formula (1) include $C_{2-6}$ straight- or branched-chain alkenyl, such as vinyl, allyl, isopropenyl, 1-butenyl, 2-butenyl, 3-butenyl, 2-methyl-2-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl, etc.

Examples of $C_{1-6}$ alkoxy represented by $R^3$ in Formula (1) include straight- or branched-chain alkoxy, such as methoxy, ethoxy, n-propoxy, isopropoxy, n-butoxy, sec-butoxy, tert-butoxy, n-pentyloxy, isopentyloxy, neopentyloxy, tert-pentyloxy, n-hexyloxy, isohexyloxy, etc.

Examples of $C_{3-8}$ cycloalkyloxy represented by $R^3$ in Formula (1) include $C_{3-8}$ cycloalkyloxy, such as cyclopropyloxy, cyclobutyloxy, cyclopenthyloxy, cyclohexyloxy, cycloheptyloxy, cyclooctyloxy, etc.

Preferable among the examples of $R^3$ are $C_{1-23}$ alkyl. Preferable as $C_{1-23}$ alkyl are $C_{1-11}$ straight- or branched-chain alkyl ($C_{1-11}$ alkyl), and more preferable are $C_{2-5}$ straight- or branched-chain alkyl ($C_{2-5}$ alkyl), such as ethyl, n-propyl, isopropyl, n-butyl, isobutyl, sec-butyl, tert-butyl, n-pentyl, isopentyl, neopentyl, tert-pentyl, etc., with $C_5$ alkyl being particularly preferable.

Sphingosine Compound (1) of the invention may form a salt with an acid.

The salt is not limited as long as it is pharmaceutically acceptable; examples of such salts include salts with inorganic acids such as hydrochloric acid, sulfuric acid, and nitric acid, and organic acids such as acetic acid and benzenesulfonic acid.

Sphingosine Compound (1) of the invention can be produced, for example, according to the steps shown in the following Reaction Scheme-1:

halogenated aromatic hydrocarbons such as chlorobenzene and dichlorobenzene; aliphatic hydrocarbons such as n-hexane, cyclohexane, and petroleum ether; aliphatic halogenated hydrocarbons such as dichloromethane, 1,2-dichloroethane, chloroform, and carbon tetrachloride; alcohols such as methanol, ethanol, and isopropyl alcohol; ethers such as diethylether, diisopropyl ether, dioxane, tetrahydrofuran (THF), ethylene glycol dimethyl ether, and ethylene glycol diethylether; ketones such as acetone, 2-butanone, and methyl isobutyl ketone; nitriles such as acetonitrile, propionitrile, and benzonitrile; amides such as N,N-dimethylformamide and hexamethylphosphoric triamide (HMPA); sulfoxides such as dimethyl sulfoxide; and mixtures thereof.

Among the above, an alcohol such as methanol is preferable as the solvent used in the first step of this reaction, and an amide such as N,N-dimethylformamide is preferable as the solvent used in the second step.

Examples of tin oxide compounds used in the first step include a tin oxide compound represented by Formula (4):

wherein $R^4$ is alkyl, cycloalkyl, or phenyl; and
a tin oxide compound represented by Formula (5):

wherein $R^5$ is alkyl, cycloalkyl, or phenyl; and $R^4$ is as defined above.

Examples of alkyl represented by $R^4$ and $R^5$ include methyl, ethyl, n-propyl, isopropyl, n-butyl, n-amyl, isoamyl, n-hexyl, n-octyl, 2-ethylhexyl, lauryl, and stearyl.

Examples of cycloalkyl represented by $R^4$ and $R^5$ include $C_{3-8}$ cycloalkyl, such as cyclopropyl, cyclobutyl, cyclopentyl, cyclohexyl, cycloheptyl, and cyclooctyl.

Specific examples of tin oxide compounds represented by Formula (4) include dimethyl tin oxide (($CH_3$)$_2$SnO), diethyl tin oxide (($C_2H_5$)$_2$SnO), dibutyltin oxide (($C_4H_9$)$_2$SnO), dioctyl tin oxide (($C_8H_{17}$)$_2$SnO), and diphenyl tin oxide (($C_6H_5$)$_2$SnO), with dimethyl tin oxide, dibutyltin oxide, and dioctyl tin oxide being preferable.

Reaction Scheme-1

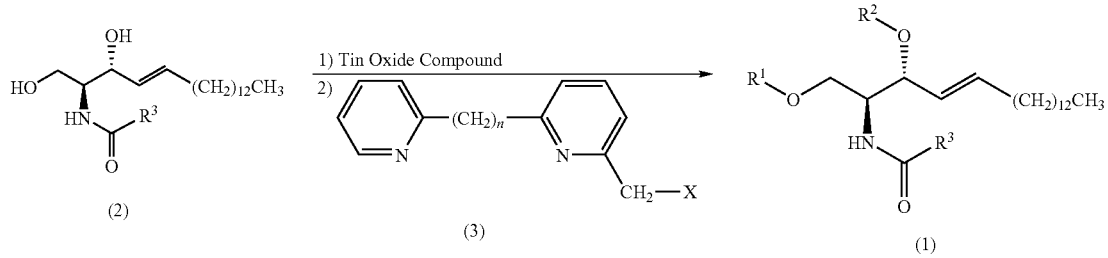

wherein $R^1$, $R^2$, $R^3$, n, and X are as defined above.

As shown in Reaction Scheme-1, Compound (1) of the invention can be produced by reacting the compound represented by Formula (2) with a tin oxide compound in a suitable solvent, followed by reacting the resulting compound with the bipyridyl compound represented by Formula (3).

That is, this reaction includes the first step of reacting Compound (2) with a tin oxide compound; and the second step of reacting the resulting compound with Compound (3).

A wide range of known solvents can be used in the first and second steps of this reaction, as long as they do not adversely affect the reaction. Examples of such solvents include aromatic hydrocarbons such as benzene, toluene, and xylene;

A specific example of tin oxide compounds represented by Formula (5) is dibutyltin dimethoxide (($C_4H_9$)$_2$Sn(OCH$_3$)$_2$).

These tin oxide compounds are commercially available, or can be produced according to a known method.

The amount of tin oxide compound is not limited as long as it is a stoichiometric quantity; generally, the amount of tin oxide compound is about 1 to about 3 moles, and preferably about 1.1 to 2 moles, per 1 mole of Compound (2).

The reaction temperature is not limited, but may generally be within the range of −10° C. to below the boiling point of the solvent used, preferably about 20 to about 100° C., and more preferably about 40 to about 80° C. The reaction time varies depending on the conditions, such as the types and amounts of the starting compounds, the reaction temperature, etc., but is generally about 0.5 to about 3 hours, and preferably about 1 to about 2 hours.

The reaction of a tin oxide compound with Compound (2) in the first step produces a stannylene compound represented by Formula (6):

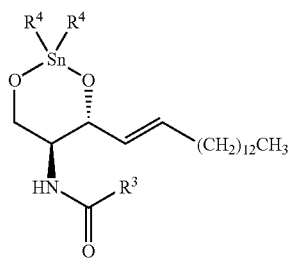

(6)

wherein $R^3$ and $R^4$ are as defined above.

The resulting stannylene compound represented by Formula (6) may be isolated and purified prior to use in the subsequent step, or may be used in the subsequent step without isolation and purification.

Moreover, the solvent in the reaction mixture obtained in the first step may be concentrated or distilled off, and a fresh solvent that is suitably selected may be added before the product is subjected to the subsequent step.

In the second step, a halogen ion is preferably present in the reaction system. To achieve this, a halide may be supplied into the reaction system.

Examples of halides include tetraalkylammonium halides such as tetrabutylammonium fluoride, tetrabutylammonium chloride, tetrabutylammonium bromide, and tetrabutylammonium iodide; and cesium fluoride. Among the above, tetrabutylammonium fluoride and cesium fluoride are preferable.

The amount of the halide used is not limited, and may be suitably selected from a wide range of amounts. The amount of the halide used is generally 1 to 5 moles, and preferably 1.1 to 2 moles, per 1 mole of Compound (2).

The amount of Compound (3) used is not limited, and may be suitably selected from a wide range of amounts. The amount of Compound (3) used is generally 0.8 to 3 moles, preferably 1.0 to 2.5 moles, and more preferably 1.1 to 1.5 moles, per 1 mole of Compound (2).

The reaction temperature is not limited, but may generally be within the range of −10° C. to below the boiling point of the solvent used, preferably about 10 to about 40° C., and more preferably about 20 to about 30° C. The reaction time varies depending on the conditions, such as the types and amounts of the starting compounds, the reaction temperature, etc., but is generally 24 hours or less, and preferably about 6 to about 12 hours.

The thus-obtained Compound (1) can be easily isolated from the reaction mixture and purified by usual isolation and purification means, e.g., column chromatography, recrystallization, etc.

In this reaction, Compound (1) is produced as a mixture of Compound (1A) and Compound (1B); these mixtures can be easily isolated and produced by a usual separation means such as HPLC. As a result, in this reaction, Compound (1A) is produced in an amount of about 4 times that of Compound (1B).

Starting Compound (2) used in Reaction Scheme-1 is easily produced according to a known method.

For example, Starting Compound (2) can be produced according to the steps shown in the following Reaction Scheme-2:

Reaction Scheme-2

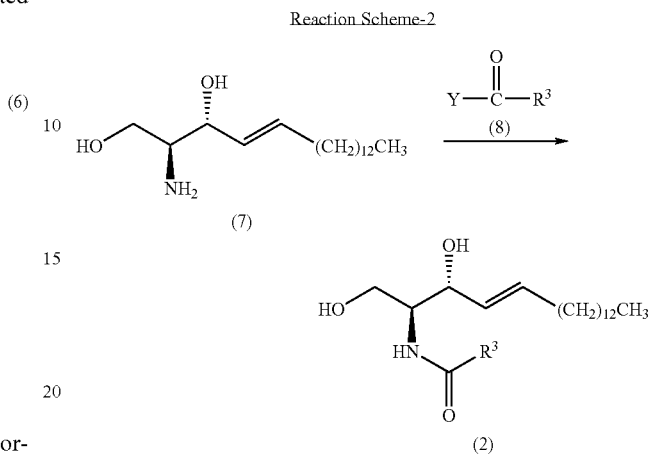

wherein $R^3$ is as defined above, and Y is halogen.

As shown in Reaction Scheme-2, Compound (2) is produced by reacting the known sphingosine represented by Formula (7) with the known carbonyl halide compound represented by Formula (8). The reaction conditions may follow a usual method for producing an amide compound by reacting a carbonyl halide and an amino compound. The Examples below describe specific examples of the reaction conditions, such as the reagents, solvents, reaction temperature, and reaction time employed in this reaction.

Starting Compound (3) used in Reaction Scheme-1 can be easily produced according to a known method.

For example, Starting Compound (3) can be produced according to the steps shown in the following Reaction Scheme-3:

Reaction Scheme-3

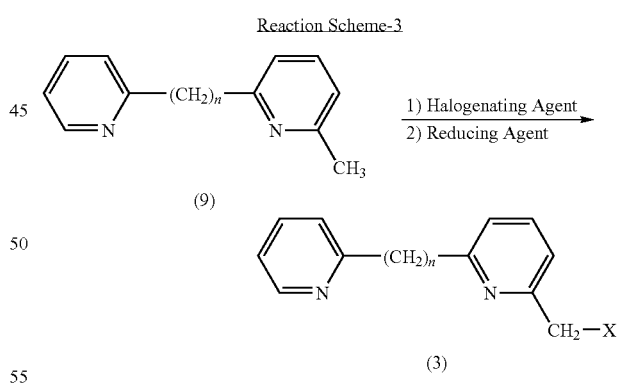

wherein n and X are as defined above.

As shown in Reaction Scheme-3, Compound (3) is produced by reacting known Compound (9) with a halogenating agent such as N-bromosuccinimide, followed by reacting the reaction product with a reducing agent for the purpose of eliminating excess substituted halogen. The reaction conditions may follow a usual method for halogenating an aromatic substituted methyl group. The Reference Examples below describe specific examples of the reaction conditions, such as the reagents, solvents, reaction temperature, and reaction time employed in this reaction.

As will be evident from the Test Examples below, Compound (1) of the invention exhibits excellent inhibitory activity against sphingomyelinase. Accordingly, Compound (1) is useful as a sphingomyelinase inhibitor, and is useful as a drug for the prevention and/or treatment of cerebral hemorrhage, cerebral infarction, and like cerebrovascular diseases, head injuries, senile dementia represented by Parkinson's disease and Alzheimer's disease, and like neurodegenerative diseases, diabetes, obesity, arteriosclerosis, inflammatory diseases, immune diseases, cancer, renal diseases, and cardiac diseases.

The invention provides a sphingomyelinase inhibitor (hereinafter also referred to as the "formulation") containing the sphingosine compound represented by Formula (1) as an active ingredient.

The formulation of the invention may solely contain Compound (1), or may be a composition that additionally contains any carriers and/or additives, and is prepared into a form suitable to a desired purpose according to a conventionally known method. Further, Compound (1) may contain one of the compounds represented by Formula (1A) and (1B), or may be a mixture of Compounds (1A) and (1B). Further, the formulation of the invention may be a composition that additionally contains any carriers and/or additives, and is prepared into a form suitable to a desired purpose according to a conventionally known method.

Examples of dosage forms of the formulation of the invention include, but are not limited to, solid formulations such as tablets, powders, granules, pills, powder syrups, and capsules (hard and soft capsules); paste or gel formulations such as creams, ointments, and gels; and liquid formulations such as solutions, suspensions, emulsions, syrups, and elixirs.

The amount of Sphingosine Compound (1) used in the formulation of the invention is not limited as long as the formulation can exhibit an inhibitory effect against sphingomyelinase. The amount of Sphingosine Compound (1) can be suitably adjusted within the range of 0.001 to 99 wt %, preferably 0.01 to 50 wt %, and more preferably 0.1 to 30 wt %, based on 100 wt % of the formulation.

The formulation may contain Compound (1) in a proportion sufficient to exhibit an inhibitory effect against sphingomyelinase, and may also contain other ingredients as long as this effect is not impaired. The other ingredients are not limited as long as they are pharmacologically and pharmaceutically acceptable. Examples of such ingredients include carriers commonly used in manufacturing pharmaceuticals, such as excipients, binders, dispersants, thickeners, lubricants, pH adjusters, and solubilizers; and antibiotics, antimicrobial agents, disinfectants, preservatives, builders, bleaching agents, enzymes, chelating agents, anti-foaming agents, coloring agents (dyes, pigments, etc.), softening agents, moisturizers, surfactants, antioxidants, flavoring agents, taste enhancers, flavor enhancers, and solvents.

Methods of using the formulation of the invention include oral administration and administration by infusion, injection, and other routes of the formulation into the body; and topical application of the formulation to an afflicted area.

The amount of the formulation of the invention will depend on the dosage form, the method of application (use), etc., and thus, cannot be generally specified. For example, a suitable daily dose of formulation calculated as the amount of Sphingosine Compound (1) is generally about 1 ng/ml to about 100 mg/ml, and preferably about 10 ng/ml to about 50 mg/ml, per 1 kg of an adult. The dose of the formulation can be suitably adjusted within this range according to the age and symptoms of the patient. The formulation may be given in one to several doses per day.

Advantageous Effects of Invention

The sphingosine compound of the invention exhibits an inhibitory activity against sphingomyelinase, and therefore can be suitably used as a drug for the prevention or treatment of cerebral hemorrhage, cerebral infarction, and like cerebrovascular diseases, head injuries, senile dementia represented by Parkinson's disease and Alzheimer's disease, and like neurodegenerative diseases, diabetes, obesity, arteriosclerosis, inflammatory diseases, immune diseases, cancer, renal diseases, and cardiac diseases.

In accordance with the method of the invention, the above-described novel sphingosine compound having a potent inhibitory activity against sphingomyelinase is provided.

DESCRIPTION OF EMBODIMENTS

Examples

The present invention will be further clarified with reference to the following Production Examples and Test Examples of Sphingosine Compound (1) of the invention; however, the invention is not limited by these Examples. In the reaction schemes shown below, Me represents a methyl group.

Reference Example 1

Synthesis of Starting Compound (7)

Starting Compound (7) can be a commercially available product, or can be synthesized according to the following known method.

(1) Reference Example 1-1

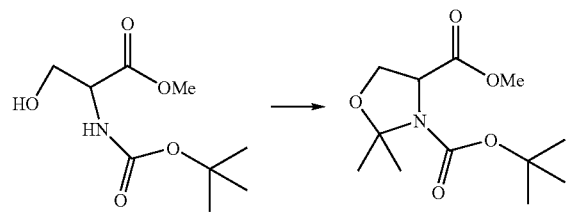

Commercially available N-tert-butoxycarbonyl-serine methyl ester (2.0 g, 9.122 mmol), 2,2-dimethoxypropane (1.9 g, 18.24 mmol), and pyridinium-p-toluene sulfonate (26 mg, 137 μmol) were dissolved in benzene (29 ml) and heated under reflux for 15 hours. A saturated sodium hydrogen carbonate solution was added to the reaction mixture, and the mixture was extracted with diethylether; the organic layer was subsequently washed with a saturated sodium chloride solution. The washed product was then dried over anhydrous magnesium sulfate and filtered, and the filtrate was subsequently concentrated. The resulting concentrate was purified by silica gel column chromatography to produce 3-tert-butyl 4-methyl 2,2-dimethyloxazolidine-3,4-dicarboxylate (2.78 g, 91% yield).

FTIR (diffuse reflectance): 2979, 1760, 1737, 1713, 1390 cm$^{-1}$

HRMS: calculated for (CI) $C_{12}H_{22}NO_5$ (M+H$^+$), 260.1498. found, 260.1495

(2) Reference Example 1-2

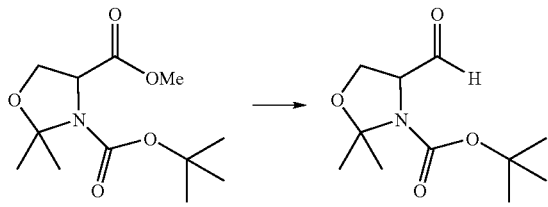

The 3-tert-butyl 4-methyl 2,2-dimethyloxazolidine-3,4-dicarboxylate (6.42 g, 24.97 mmol) obtained in the above-described reaction was dissolved in toluene (50 ml) and cooled to −78° C.; subsequently, a toluene solution of diisobutylaluminum hydride (0.93 M) was slowly added dropwise. After 30 minutes, methanol was added to the mixture and the reaction was stopped; a 10% potassium sodium tartrate solution (150 ml) was further added, and the mixture was extracted with ethyl acetate. The organic layer was dried over anhydrous magnesium sulfate, filtered and concentrated. The resulting concentrate was purified by silica gel column chromatography to produce tert-butyl 4-formyl-2,2-dimethyloxazolidine-3-carboxylate (4.22 g, 74% yield).

FTIR (diffuse reflectance): 3449, 2978, 1737, 1694, 1366, 1258, 1172 cm$^{-1}$

HRMS: calculated for (CI) $C_{11}H_{20}NO_4$ (M+H$^+$), 230.1392. found, 230.1390

(3) Reference Example 1-3

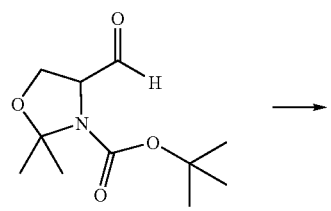

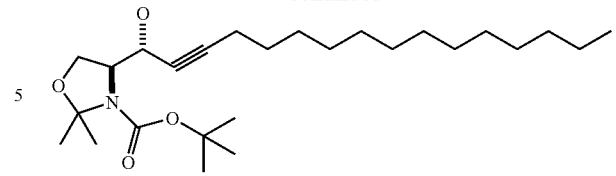

1-Pentadecyne (1.7 g, 8.17 mmol) was dissolved in tetrahydrofuran (THF) (7.5 ml) and cooled to 0° C. An n-hexane solution of n-butyllithium (7.6 ml, 7.85 mmol) was slowly added dropwise to this solution. After 90 minutes of stirring, a THF solution (75 ml) of the tert-butyl 4-formyl-2,2-dimethyloxazolidine-3-carboxylate (1.0 g, 4.36 mmol) obtained in the above-described reaction was added at −40° C., and the mixture was further stirred for 20 minutes. A saturated ammonium chloride solution was added to the resulting mixture, and the reaction was stopped; the mixture was subsequently extracted with diethylether, and the organic layer was washed with a saturated sodium chloride solution, dried and concentrated. The concentrate was purified by silica gel column chromatography to produce (S)-tert-butyl 4-((R)-1-hydroxy-2-hexadecynyl)-2,2-dimethyloxazolidine-3-carboxylate) (1.2 g, 49% yield).

(4) Reference Example 1-4

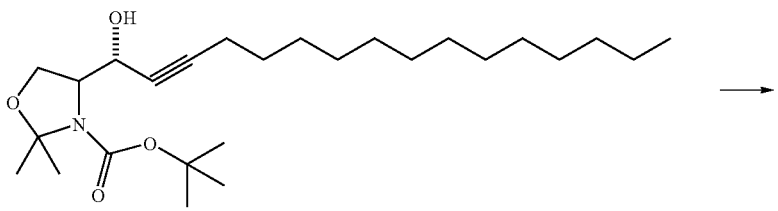

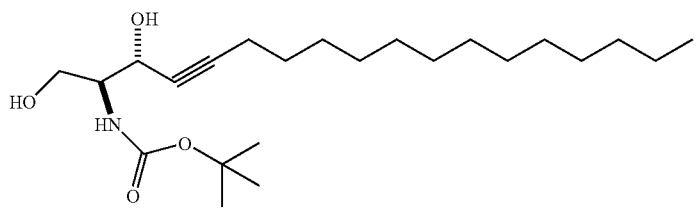

The (S)-tert-butyl 4-((R)-1-hydroxy-2-hexadecynyl)-2,2-dimethyloxazolidine-3-carboxylate) (100 mg, 0.23 mmol) obtained in the above-described reaction was dissolved in methanol (4.4 ml); p-toluenesulfonic acid (0.8 mg, 4.6 µmol) was added to the solution, and the mixture was stirred at room temperature for 12 hours. P-toluenesulfonic acid (0.8 mg, 4.6 µmol) was added to this reaction mixture, stirred for 6 hours, heated to 60° C., and further stirred for 2 hours. Saturated sodium hydrogen carbonate was added to this reaction mixture, and the reaction was stopped; the mixture was subsequently extracted with ethyl acetate, and the organic layer was dried and filtered. The resulting filtrate was purified by column chromatography to produce tert-butyl (2S,3R)-1,3-dihydroxyoctadec-4-yn-2-ylcarbamate (85 mg, 93% yield).

FTIR (diffuse reflectance): 3449, 2926, 2854, 1703, 1458, 1394, 1366 cm$^{-1}$

HRMS (FAB): calculated for $C_{23}H_{43}NO_4Na$ (M+Na$^+$), 420.3089. found, 420.3058

(5) Reference Example 1-5

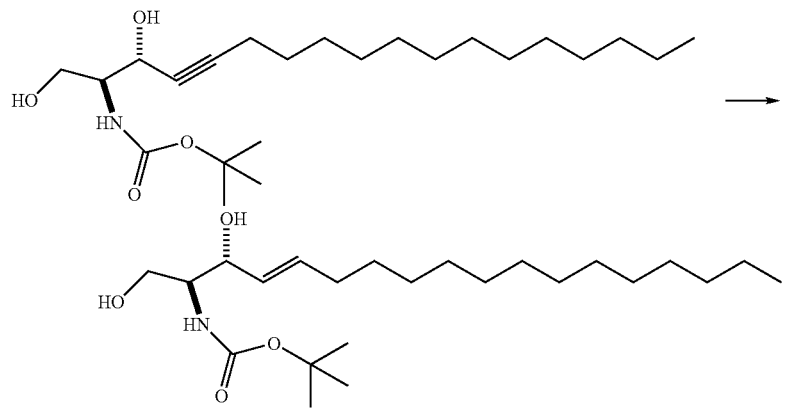

The tert-butyl (2S,3R)-1,3-dihydroxyoctadec-4-yn-2-yl-carbamate (85 mg, 0.21 mmol) obtained in the above-described reaction was dissolved in THF (21 ml) and cooled to 0° C.; a 65% toluene solution of sodium bis(2-methoxyethoxy)aluminium hydride (Red-Al) (258 μl, 0.850 mmol) was subsequently added dropwise. The resulting mixture was heated to room temperature and stirred for 2.5 hours. 1 M hydrochloric acid was subsequently added to the mixture, and the reaction was stopped; the mixture was extracted with diethylether, and the organic layer was dried over anhydrous sodium sulfate, filtered and concentrated. The concentrate was purified by silica gel column chromatography to produce N-tert-butoxycarbonyl sphingosine (52 mg, 64%).

FTIR (diffuse reflectance): 3370, 2924, 2853, 1689, 1508, 1170 cm$^{-1}$

HRMS: calculated for (CI) $C_{23}H_{46}NO_4$ (M+H$^+$), 400.3427. found, 400.3433

(6) Reference Example 1-6

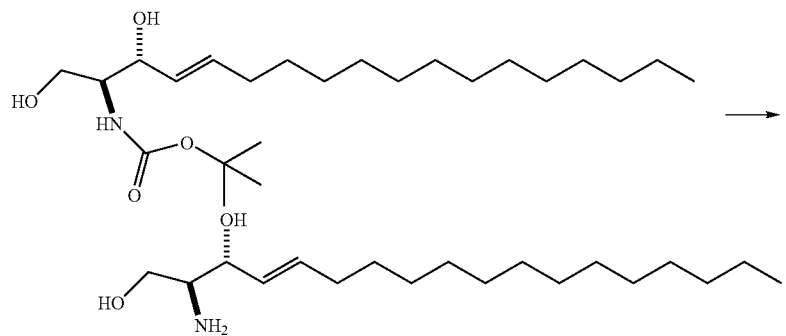

N-tert-butoxycarbonyl sphingosine (100 mg, 0.25 mmol) was dissolved in 6 M hydrochloric acid/THF (1:5), and stirred at room temperature for 2 hours. The resulting mixture was heated to 50° C. and stirred for 16 hours. The mixture was neutralized with a 10% sodium hydroxide solution and extracted with dichloromethane, and the product was dried over anhydrous sodium sulfate, filtered and concentrated. The resulting crude crystals were re-crystallized using n-hexane to produce Starting Compound (7) (74 mg, 98% yield).

Physical Properties of Starting Compound (7):

FTIR (diffuse reflectance): 3352, 2921, 2951, 1614, 1472, 1383 cm$^{-1}$

HRMS: calculated for (CI) $C_{18}H_{38}NO_2$ (M+H$^+$), 300.2902. found, 300.2903

Reference Example 2

Synthesis Example of Compound (3)

(1) Reference Example 2-1

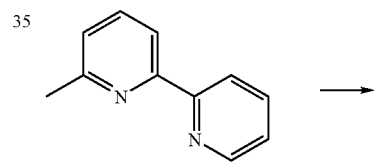

-continued

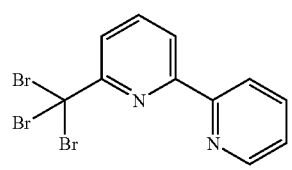

Commercially available 6-methyl-2,2'-bipyridine (200 mg, 1.17 mmol) was dissolved in carbon tetrachloride; N-bromosuccinimide (1.4 g, 5.85 mmol) and 2,2'-azobis isobutyronitrile (13.5 mg, 82.32 µmol) were added to the solution, and the mixture was heated under reflux for 12 hours. After cooling to room temperature, a saturated sodium chloride solution was added, the resulting mixture was extracted with dichloromethane, and the organic layer was dried over anhydrous sodium sulfate, filtered and concentrated. The concentrate was purified by silica gel column chromatography to produce 6-tribromomethyl-2,2'-bipyridine in a quantitative yield as colorless crystals. The subsequent reduction reaction was performed using the 6-tribromomethyl-2,2'-bipyridine.

(2) Reference Example 2-2

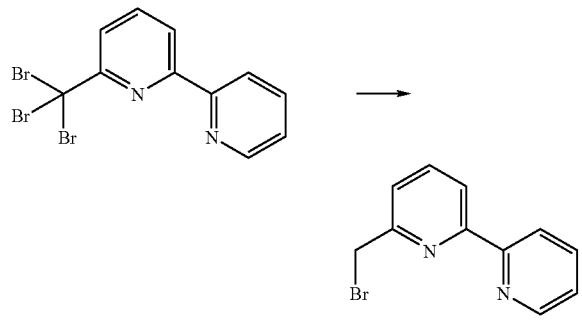

The 6-tribromomethyl-2,2'-bipyridine (205 mg, 503.8 mmol) was dissolved in dichloromethane (5 ml) and cooled to −78° C.; a dichloromethane solution of diisobutylaluminum hydride (DIBAL) (0.97 M, 1.5 ml) was subsequently added dropwise. After the consumption of the starting material was confirmed by TLC, methanol was added, and the reaction was stopped. The reaction mixture was heated to 0° C., and a 10% potassium sodium tartrate solution was subsequently added. The resulting mixture was extracted with diethylether, and the product was washed with a saturated sodium chloride solution, dried over anhydrous sodium sulfate, filtered and concentrated. The concentrate was purified by silica gel column chromatography to produce Compound (3-1) (6-bromomethyl-2,2'-bipyridine) (54 mg, 54% yield).

Physical Properties of Compound (3-1):
$^1$H NMR (200 MHz, CDCl$_3$) δ 4.63 (s, 2H), 7.27-7.33 (ddd, J=7.8, 4.6, 1.0 Hz, 1H), 7.45 (dt, J=7.8, 1.0 Hz, 1H), 7.80 (t, J=7.8 Hz, 2H), 8.31 (dd, J=7.8, 1.0 Hz, 1H), 8.45 (dt, J=7.8, 1.0 Hz, 1H), 8.67 (m, 1H)
$^{13}$C NMR (50 MHz, CDCl$_3$) δ 34.14, 120.22, 121.32, 123.35, 123.85, 136.89, 137.89, 149.13, 155.66, 155.88, 156.20 cm$^{-1}$
FTIR (diffuse reflectance): 3024, 2924, 2853, 1581, 1492, 1454, 1429 cm$^{-1}$
HRMS: calculated for C$_{11}$H$_9$N$_2$Br (M$^+$), 247.9949. found, 247.9967

Production Example 1
Production Example of Sphingosine Compound (1)
(1) Production Example 1-1

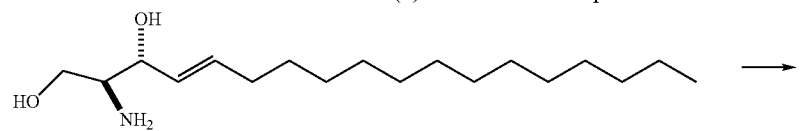

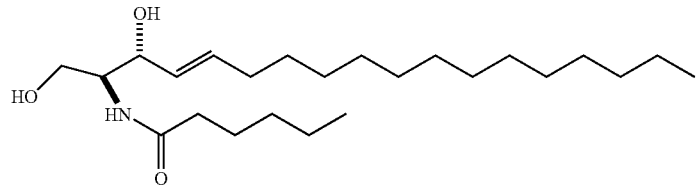

Starting Compound (7) (97 mg, 326 µmol), 4-dimethylaminopyridine (1 mg), and triethylamine (10 µl) were dissolved in dichloromethane (3 ml), and cooled to 0° C.; a dichloromethane solution of hexanoyl chloride (40 mg, 297 µmol, CH$_2$Cl$_2$ 3 ml) was subsequently added. After 10 minutes, a saturated sodium hydrogen carbonate solution was added, and the mixture was extracted with dichloromethane. The resulting organic layer was dried over anhydrous magnesium sulfate, filtered and concentrated.

The concentrate was purified by silica gel column chromatography to produce ceramide (67 mg, 57%).

Physical Properties of Ceramide:
$^1$H NMR (200 MHz, CDCl$_3$) δ 0.88 (t, J=6.2 Hz, 3H), 0.90 (t, J=6.2 Hz, 3H), 1.22-1.40 (m, 28H), 1.63 (m, 2H), 2.22 (t, J=7.4 Hz, 2H), 3.60-3.73 (m, 2H), 3.88-3.92 (m, 2H), 4.27 (m, 1H), 5.50 (dd, J=6.4, 15.4 Hz, 1H), 5.76 (t, J=6.6, 15.4 Hz, 1H), 6.47 (br d, J=7.4 Hz, 1H)
$^{13}$C NMR (50 MHz, CDCl$_3$) δ 13.86q, 14.10q, 22.33t, 22.61t, 25.39t, 29.14t, 29.22t, 29.29t, 29.46t, 29.59t (2C), 29.64t (3C), 31.37t, 31.86t, 32.27t, 36.68t, 54.63d, 62.21t, 74.07d, 128.85d, 133.87d, 174.08s
FTIR (diffuse reflectance): 3297, 2920, 3251, 1645, 1542 cm$^{-1}$
HRMS (FAB): calculated for C$_{24}$H$_{47}$N$_1$O$_3$Na (M+Na$^+$), 420.3454. found, 420.3437

(2) Production Example 1-2

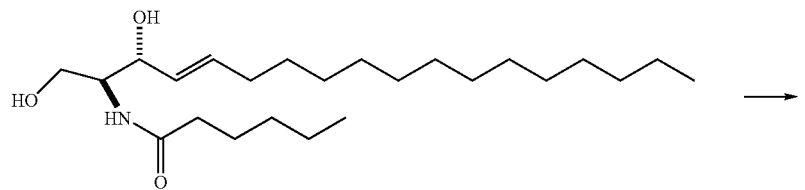

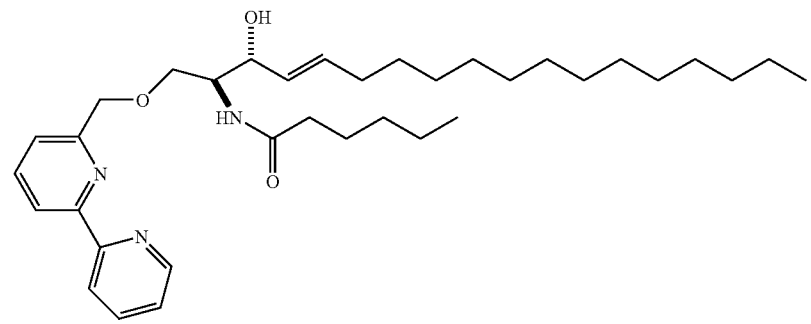

1a

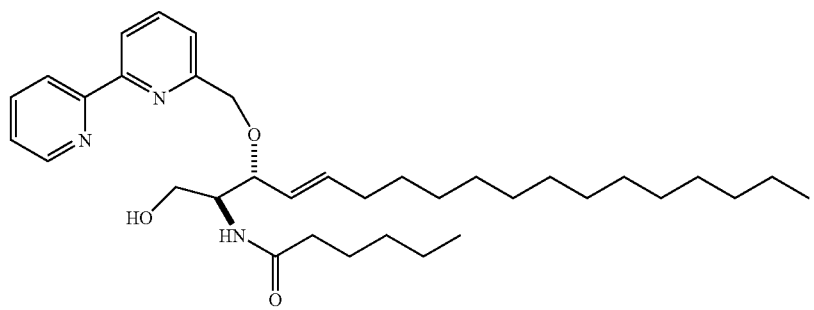

1b

Ceramide (67 mg, 168.5 μmol) was dissolved in methanol (1.7 ml), and dibutyltin oxide (42.4 mg, 170.2 μmol) was added to the solution and heated under reflux for 1 hour. After cooling to room temperature, the methanol was distilled off under reduced pressure, and anhydrous N,N-dimethylformamide (DMF) (1.9 ml) was added. Compound (3-1) (46 mg, 185 μmol) and tetra-n-butylammonium fluoride (1M THF, 185 μl) were further added, and the mixture was stirred at room temperature for 24 hours. Water was added to the reaction mixture, and the reaction mixture was extracted with ethyl acetate; the organic layer was subsequently dried over anhydrous sodium sulfate, filtered and concentrated. The concentrate was purified by silica gel column chromatography to produce the target compound as a mixture of Compound (1a) and Compound (1b) (27.5 mg, 29% yield). This mixture was purified by high-performance liquid chromatography (HPLC) (ODS, methanol:water=10:1) to produce Compound (1a) and Compound (1b) in a ratio of 4:1.

Physical Properties of Compound (1a):

$^1$H NMR (200 MHz, CDCl$_3$) δ 0.87 (t, J=6.2 Hz, 6H), 1.25-1.32 (m, 24H), 1.58 (m, 2H), 1.99 (m, 2H), 2.18 (t, J=7.6 Hz, 2H), 3.73 (m, 1H), 3.78 (dd, J=9.6, 3.8 Hz, 1H), 3.94 (dd, J=9.6, 3.8 Hz, 1H), 4.11 (m, 1H), 4.14 (m, 1H), 4.65 (d, J=12.8 Hz, 1H), 4.74 (d, J=12.8 Hz, 1H), 5.49 (dd, J=15.4, 5.2 Hz, 1H), 5.73 (dt, J=15.4, 6.8 Hz, 1H), 6.35 (d, J=7.8 Hz, 1H), 7.31 (m, 2H), 7.83 (t, J=7.8 Hz, 2H), 8.33 (d, J=7.8 Hz, 1H), 8.42 (d, J=7.8 Hz, 1H), 8.67 (br d, J=4.6 Hz, 1H)

$^{13}$C NMR (50 MHz, CDCl$_3$) δ 13.94, 14.13, 22.40, 22.70, 25.44, 29.22 (C2), 29.22, 29.37, 29.51-29.70 (5C), 31.43, 31.94, 32.29, 36.80, 52.93, 70.67, 74.27, 74.37, 120.24, 121.26, 121.48, 123.85, 129.19, 133.41, 136.97, 137.61, 149.24, 155.90, 156.04, 156.93, 173.36

FTIR (diffuse reflectance): 3279, 2954, 2919, 2851, 1635, 1546, 1430 cm$^{-1}$

HRMS: calculated for (CI) C$_{35}$H$_{56}$N$_3$O$_3$ (M+H$^+$), 566.4321. found, 566.4321

Physical Properties of Compound (1b):

$^1$H NMR (300 MHz, CDCl$_3$) δ 0.85 (t, J=6.6 Hz, 3H), 0.87 (t, J=6.6 Hz, 3H), 1.24-1.36 (m, 24H), 1.55 (m, 2H), 2.07 (m, 4H), 3.61 (m, 2H), 4.01 (m, 1H), 4.09 (m, 2H), 4.54 (d, J=13.2 Hz, 1H), 4.80 (d, J=13.2 Hz, 1H), 5.47 (dd, J=7.8, 15.6 Hz, 1H), 5.80 (dt, J=6.6, 15.6 Hz, 1H), 6.31 (d, J=8.1 Hz, 1H), 7.27-7.34 (m, 2H), 7.82 (m, 2H), 8.27 (d, J=7.8 Hz, 1H), 8.36 (d, J=7.8 Hz, 1H), 8.67 (br d, J=5.1 Hz, 1H)

$^{13}$C NMR (50 MHz, CDCl$_3$) δ 13.90, 14.13, 22.38, 22.70, 25.36, 29.11, 29.23, 29.37, 29.49, 29.70 (5C), 31.39, 31.93, 32.35, 36.75, 53.80, 62.20, 71.18, 82.43, 120.29, 121.32, 121.66, 123.88, 126.22, 137.02, 137.37, 137.63, 149.30, 155.92, 156.15, 157.51, 173.67

HRMS (FAB): calculated for $C_{35}H_{55}N_3O_3Na$ (M+Na$^+$), 588.4141. found, 588.4160

Test Example 1

Measurement of Inhibitory Effect

Preparation of 0.2 M Tris Buffer (pH 7.5) (TB)

24.2 g of tris (Nacalai code: 35434-34) was dissolved in 1,000 ml of distilled water (DW), and adjusted to pH 7.5 with hydrochloric acid.

Preparation of Tris Buffer Saline (TBS)

9 g of sodium chloride (NaCl) was added to 100 ml of TB, and adjusted to a total volume of 1,000 ml with DW.

Preparation of Gelatin Tris Buffer Saline (GTBS)

4.5 g of NaCl and 1.25 g of gelatin (Merck code: 1.04078.0500) were added to 50 ml of 0.2 M TB (pH 7.5), and adjusted to a total volume of 500 ml with DW.

Washing of Sheep Erythrocyte

Preserved sheep blood; Nippon Biotest Labo, code: 0101-1

1.0 ml of preserved sheep blood was suspended in TBS and centrifuged for 3 minutes at 2,500 rpm, and the supernatant was removed. The same centrifugal operation as above was repeated a total of three times, and the precipitate was suspended in 1.5 ml of TBS to prepare a washed erythrocyte solution.

Preparation of Sphingomyelin-Liposome (SM-Liposome)

The sphingomyelin (SM), cholesterol, and CF solution used were as follows:

SM: sphingomyelin from bovin brain, code: 32156-74

Cholesterol: Nakarai code: 08721-75

CF solution: 5(6)-carbosyfluorescein; SIGMA C8166, FW=460.4

About 100 µl of 1 N sodium hydroxide (NaOH) was added to CF (27 mg/3 ml, DW) to prepare a CF solution. At this time, NaOH was added to give a pH of 7 to 8 as measured by a pH test paper.

Liposome Preparation Method

59 µl of a solution obtained by dissolving 2 mg of sphingomyelin (SM) in 160 µl of a mixed solvent of chloroform ($CHCl_3$) and methanol (MeOH) ($CHCl_3$:MeOH=2:1) was mixed with 20 µl of a solution obtained by dissolving 19.3 mg of cholesterol in 1 ml of $CHCl_3$; the mixture was homogeneously spread to the bottom of a glass test tube while the $CHCl_3$ and MeOH were distilled under nitrogen, and dried in a desiccator for 30 minutes. The CF solution was warmed to 55° C., and 80 µl of the CF solution was added with stirring to the SM from which the solvent was distilled (the molar ratio of cholesterol to CF solution: 1:1), and a procedure of placing the mixture in a water bath at 55° C. and stirring the mixture was repeated three times at 30-second intervals. A suitable amount of TBS was added, the mixture was centrifuged for 20 minutes at 15,000 rpm and 4° C., and the supernatant was removed. A suspension of the resulting product in 300 µl of TBS was used as a liposome.

Experiment 1: Influence of Compound (1a) and Compound (1b) on the Hemolytic Activity of *Bacillus cereus*-SMase (i) Solution of Compound (1a)

Compound (1a) was dissolved in MeOH and adjusted to 1.7 mM and 17 mM.

(ii) Solution of Compound (1b)

Compound (1b) was dissolved in MeOH and adjusted to 1.7 mM and 17 mM.

[Method] 30 ng/ml *Bacillus cereus*-SMase was mixed with the solution of Compound (1a) with each concentration or the suspension of Compound (1b) with each concentration, and the mixture was adjusted with GTBS (pH 5.5) to a total volume of 240 µl and pre-treated for 10 minutes at 37° C., after which 60 µl of the washed sheep erythrocyte ($6\times10^{11}$ cells/(ml)) was added to the resulting reaction mixture and incubated for 30 minutes at 37° C. After cooling in ice for 10 minutes at 4° C., TBS was added to the product and the resulting product was centrifuged for 3 minutes at 2,500 rpm; the supernatant was dispensed into a 96-well microplate, and the absorbance ($O.D._{550}$) was measured (Corona Electric Co., Ltd.; MTP32 Microplate Reader).

TABLE 1

Influence of Compound (1a) and Compound (1b) on Sheep Erythrocyte Hemolysis of *Bacillus cereus*-SMase

| Inhibitor | Concentration (µM) | Sphingomyelinase Activity (%) |
|---|---|---|
| Control | | 100 |
| Compound (1a) | 1 | 98.2 ± 1.4 |
| | 5 | 76.4 ± 4.3 |
| | 10 | 54.4 ± 3.1 |
| | 100 | 32.7 ± 2.5 |
| Compound (1b) | 1 | 96.2 ± 2.7 |
| | 5 | 86.5 ± 3.3 |
| | 10 | 82.7 ± 4.2 |
| | 100 | 78.8 ± 2.3 |

As shown in Table 1, as the concentration of the solution of Compound (1a) was increased to 1, 5, 10, and 100 µM, the sphingomyelinase activity was inhibited as the concentration was increased; when a 100-µM solution of Compound (1a) was added, the sphingomyelinase activity was inhibited by about 30%. On the other hand, Compound (1b) did not show as potent an inhibitory effect as Compound (1a).

Experiment 2: Influence of Compound (1a) and Compound (1b) on SM-Liposome Degradation Activity of *Bacillus cereus*-SMase (i) Solution of Compound (1a)

Compound (1a) was dissolved in MeOH and adjusted to 1.7 mM and 17 mM.

(ii) Solution of Compound (1b)

Compound (1b) was dissolved in MeOH and adjusted to 1.7 mM and 17 mM.

[Method] Bc-SMase (50 ng/ml) was mixed with the solution of Compound (1a) with each concentration or the solution of Compound (1b) with each concentration, and the mixture was adjusted with GTBS (pH 5.5) to a total volume of 180 µl and pre-treated for 10 minutes at 37° C., after which 20 µl of the SM-liposome was added to the resulting reaction mixture and incubated for 30 minutes at 37° C. The reaction mixture was measured using a fluorometer (Corona Electric Co., Ltd.; MTP32 Microplate Reader, $Ex_{490}$, $Em_{530}$).

TABLE 2

Influence of Compound (1a) and Compound (1b) on SM-Liposome Degradation Activity of *Bacillus cereus*-SMase

| Inhibitor | concentration (µM) | Sphingomyelinase Activity (%) |
|---|---|---|
| Control | | 100 |
| Compound (1a) | 1 | 99.0 ± 0.2 |
| | 5 | 49.4 ± 1.4 |
| | 10 | N.D. |
| | 100 | N.D. |

TABLE 2-continued

Influence of Compound (1a) and Compound (1b) on SM-Liposome Degradation Activity of *Bacillus cereus*-SMase

| Inhibitor | concentration (μM) | Sphingomyelinase Activity (%) |
|---|---|---|
| Compound (1b) | 1 | 99.1 ± 0.3 |
| | 5 | 97.2 ± 1.1 |
| | 10 | 96.4 ± 1.7 |
| | 100 | 72.9 ± 3.2 |

N.D.: Not Detected

As shown in Table 2, as the concentration of the solution of Compound (1a) was increased to 1, 5, 10, and 100 μM, the sphingomyelinase activity was inhibited as the concentration was increased; when a 100-μM solution of Compound (1a) was added, the sphingomyelinase activity was substantially completely inhibited. On the other hand, Compound (1b) did not show as potent an inhibitory effect as Compound (1a).

Experiment 3: Influence of Compound (1a) and Compound (1b) on the $^{14}$C-Sphingomyelin ($^{14}$C-Sphingomyelin) Decomposition Activity of *Bacillus cereus*-SMase (i) Solution of Compound (1a)

Compound (1a) was dissolved in MeOH and adjusted to 1.7 mM and 17 mM.

(ii) Solution of Compound (1b)

Compound (1b) was dissolved in MeOH and adjusted to 1.7 mM and 17 mM.

(iii) Preparation of TX-Buffer 0.5 g of Triton X-100 was dissolved in 100 ml of 0.02 M TB.

[Method] 30 ng/ml *Bacillus cereus*-SMase was mixed with the solution of Compound (1a) with each concentration or the solution of Compound (1b) with each concentration, and the mixture was adjusted with TX-buffer (pH 5.5) to a total volume of 200 μl and pre-treated for 10 minutes at 37° C., after which 10 μl of $^{14}$C-sphingomyelin was added to the reaction mixture, and the resulting mixture was incubated for 30 minutes at 37° C. 600 μl of a solvent to stop the reaction (stop solution; CHCl$_3$:MeOH=1:2) was added to the reaction mixture and the resulting mixture was stirred for 30 seconds twice, and centrifuged for 20 minutes at 2,000 rpm, after which the upper layer was measured using a liquid scintillation counter.

TABLE 3

Influence of Compound (1a) and Compound (1b) on $^{14}$C-Sphingomyelin ($^{14}$C-Sphingomyelin) Decomposition Activity of *Bacillus cereus*-SMase

| Inhibitor | Concentration (μM) | Sphingomyelinase Activity (%) |
|---|---|---|
| Control | | 100 |
| Compound (1a) | 1 | 98.6 ± 1.3 |
| | 5 | 56.6 ± 1.6 |
| | 10 | 50.1 ± 2.5 |
| | 100 | 25.6 ± 1.5 |
| Compound (1b) | 1 | 98.2 ± 2.3 |
| | 5 | 88.7 ± 1.3 |
| | 10 | 84.8 ± 4.0 |
| | 100 | 76.8 ± 2.5 |

As shown in Table 3, as the concentration of the solution of Compound (1a) was increased to 1, 5, 10, and 100 μM, the sphingomyelinase activity was inhibited as the concentration was increased; when a 100-μM solution of Compound (1a) was added, the sphingomyelinase activity was inhibited by about 25%. On the other hand, Compound (1b) did not show as potent an inhibitory effect as Compound (1a).

The invention claimed is:

1. A sphingosine compound or a salt thereof represented by Formula (1):

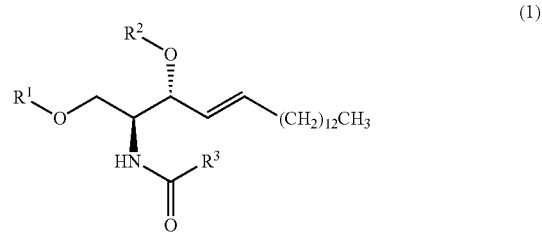

wherein one of $R^1$ and $R^2$ is hydrogen, and the other is a group represented by Formula (G):

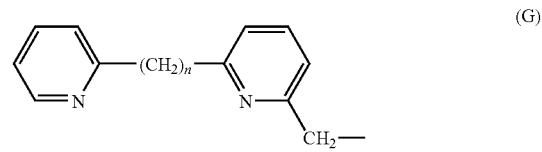

wherein n is 0 or 1; and $R^3$ is hydrogen, $C_{1-23}$ alkyl, $C_{3-8}$ cycloalkyl, $C_{2-6}$ alkenyl, $C_{1-6}$ alkoxy, $C_{3-8}$ cycloalkyloxy, phenyl, or furil.

2. The sphingosine compound or a salt thereof according to claim 1, wherein $R^1$ is a group represented by Formula (G), and $R^2$ is hydrogen.

3. The sphingosine compound or a salt thereof according to claim 1, wherein $R^1$ is hydrogen, and $R^2$ is a group represented by Formula (G).

4. A method for producing a sphingosine compound or a salt thereof represented by Formula (1):

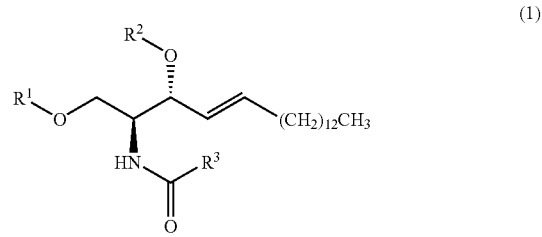

wherein one of $R^1$ and $R^2$ is hydrogen, and the other is a group represented by Formula (G):

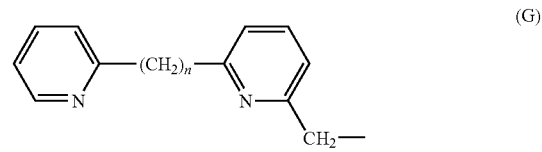

wherein n is 0 or 1; and $R^3$ is hydrogen, $C_{1-23}$ alkyl, $C_{3-8}$ cycloalkyl, $C_{2-6}$ alkenyl, $C_{1-6}$ alkoxy, $C_{3-8}$ cycloalkyloxy, phenyl, or furil; the method comprising:

reacting a tin oxide compound with a compound represented by Formula (2):

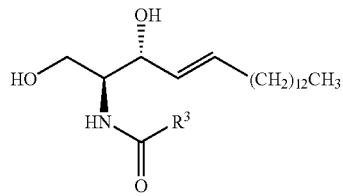

(2)

wherein $R^3$ is hydrogen, $C_{1-23}$ alkyl, $C_{3-8}$ cycloalkyl, $C_{2-6}$ alkenyl, $C_{1-6}$ alkoxy, $C_{3-8}$ cycloalkyloxy, phenyl, or furil; and reacting the resulting compound with a bipyridyl compound represented by Formula (3):

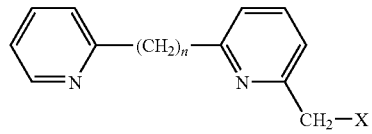

(3)

wherein n is 0 or 1, and X is halogen.

5. A sphingomyelinase inhibitor containing a sphingosine compound or a salt thereof represented by Formula (1):

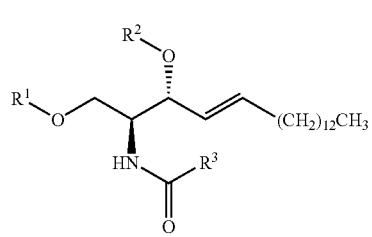

(1)

wherein one of $R^1$ and $R^2$ is hydrogen, and the other is a group represented by Formula (G):

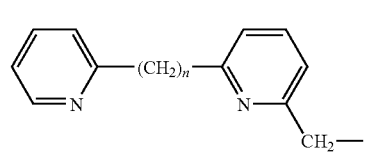

(G)

wherein n is 0 or 1; and $R^3$ is hydrogen, $C_{1-23}$ alkyl, $C_{3-8}$ cycloalkyl, $C_{2-6}$ alkenyl, $C_{1-6}$ alkoxy, $C_{3-8}$ cycloalkyloxy, phenyl, or furil.

* * * * *